Feb. 23, 1960 F. MEILLAND Plant Pat. 1,913
ROSE PLANT
Filed Jan. 8, 1959
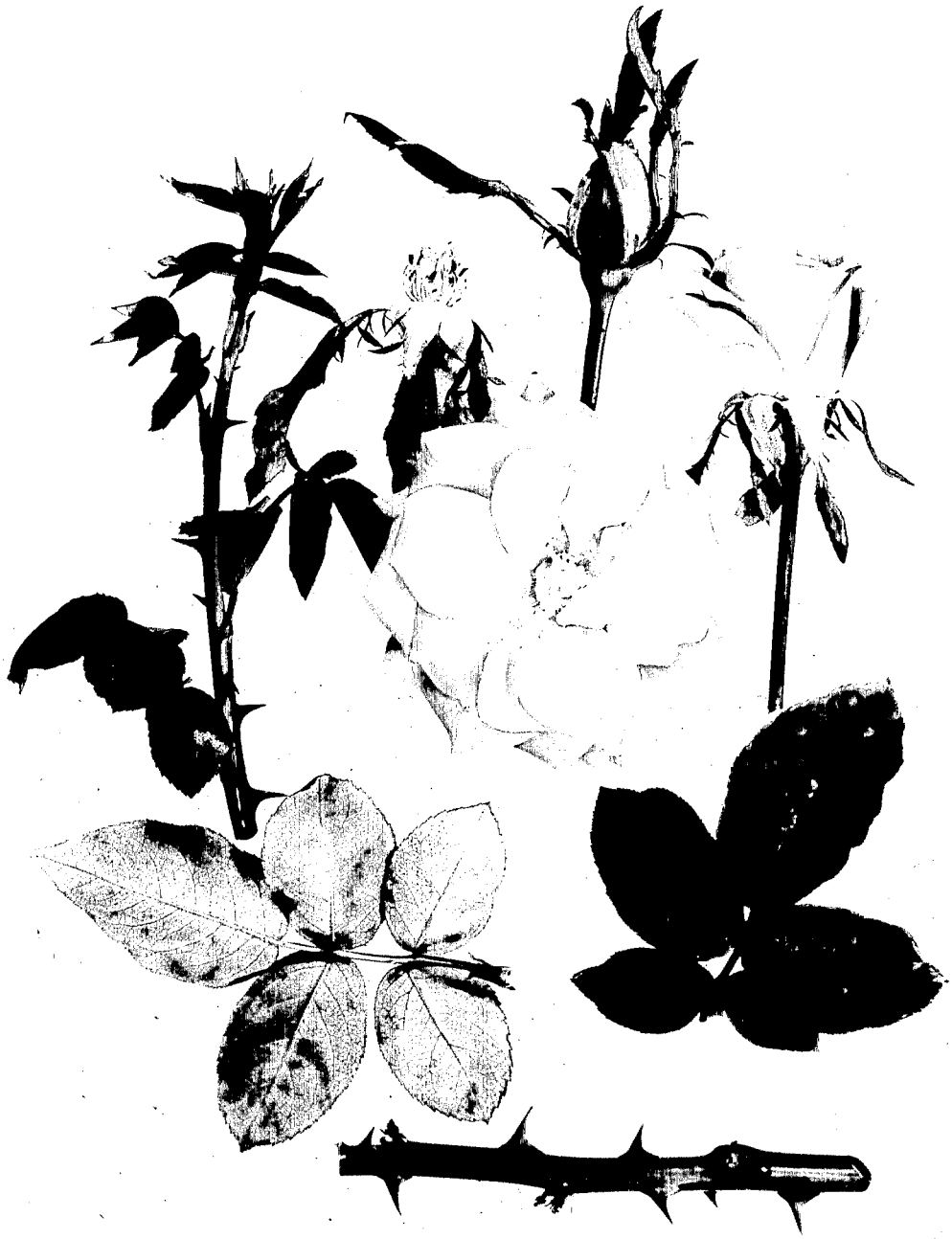
Inventor.
Francis Meilland, Deceased
By: Marie Louise Meilland, née Paolino
Legal Representative
By: Robb & Robb, Attorneys United States Patent Office Plant Pat. 1,913
Patented Feb. 23, 1960

1,913

ROSE PLANT

Francis Meilland, deceased, late of Cap d'Antibes, France, by Marie Louise Meilland, nee Paolino, legal representative, Cap d'Antibes, France Application January 8, 1959, Serial No. 785,769

Claims priority, application France June 10, 1958

1 Claim. (Cl. 47—61)

The present invention relates to a new and distinct variety of rose plant of the hybrid tea class, which was originated by the deceased by crossing an unnamed and unpatented seedling of "Pigalle" (unpatented)×"Prelude" (unpatented) with an unnamed and unpatented seedling of "Prelude"×"Pigalle."

The primary objective of this breeding was to achieve a re-grouping and further development of new and different petal pigments which were evident in previous planned crossings in this strain, while at the same time attaining improvements in flower form and habit of growth. These objectives were fully achieved by a carefully planned inbreeding program of the parent varieties aforementioned, as evidenced by the following unique combination of characteristics which are outstanding in the new variety and definitely differentiate it from its parents as well as from all other varieties of which the deceased was aware:

(1) A sufficiently vigorous and balanced habit of growth which is suitable for garden decoration;

(2) An improved bloom form which is superior to that of either parent; and (3) A Burnt Orange general color tonality of the flower petals, shading from a varying Yellow Ochre to Indian Yellow at their base, which, when viewed in combination, give a general color effect which is completely unique to the genus Rosa.

Asexual reproduction of the new variety by budding, as performed in France and also at West Grove, Pennsylvania, U.S.A., shows that the foregoing characteristics and distinctions come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of the new variety, with color terminology in accordance with the Horticultural Colour Chart of the British Colour Council, except where general color terms of ordinary dictionary significance are obvious:

Type: Hardy; bush; outdoor; seedling; for cut flowers and for garden decoration.
Class: Hybrid tea.
Breeding: Seedling.
*Seed parent.*—An unnamed and unpatented seedling of "Pigalle"×"Prelude."
*Polen parent.*—An unnamed and unpatented seedling of "Prelude"×"Pigalle."
Propagation: Holds its distinguishing characteristics through succeeding propagations by budding.

*Flower*

Locality where grown and observed: West Grove, Pennsylvania, U.S.A.
Flowers borne: Singly to stem; on stems of normal strength and medium length.

Quantity of bloom: Free, outdoors.
Continuity: Continuous.
Fragrance: From slight to moderate. Nature—tea.
Bud:
*Peduncle.*—Medium length; medium caliper; erect; stiff; smooth.—Fern Green, Plate 0862, overlaid with Oxblood Red, Plate 00823/3 where exposed to sun.
*Before calyx breaks.*—Size—medium. Form—medium length; pointed-ovoid; with a conspicuous neck; with foliaceous appendages on the surface of the bud; with stout, much-cut foliaceous parts extending beyond the tip of the bud equal to ½ or more of its length.
*As calyx breaks.*—Color—Apricot, Plate 609/2.
*As first petal opens.*—Size—medium. Form—medium length; urn-shaped. Color: outside—Mars Orange, Plate 013/2 at outer edge, shading to Salmon, Plate 412, with basal area Dresden Yellow, Plate 64/2, veined with Scheeles Green, Plate 860/3; inside—Burnt Orange, Plate 014/2, tinting to Carrot Red, Plate 612/2 at center of petal, with basal area Dresden Yellow, Plate 64/1.
*Opening.*—Opens up well.
Bloom:
*Size (when fully open).*—Medium; from 3¼ inches to 3½ inches.
*Petalage.*—Double; from 40 to 55 petals; arranged regularly.
*Form.*—Cupped and high-centered at first, but becoming globular; petals at first being loosely rolled outward, and remaining loosely rolled outward at maturity.
Petals: Medium thickness; with inside satiny and outside satiny. Shape: outer—obovate; intermediate—obovate; inner—broadly obovate.

This description of a newly opened flower was made from a rose grown outdoors in the month of August at West Groove, Pennsylvania, U.S.A.:

*Color.*—Outer petal: outside surface—Burnt Orange, Plate 014/3 at outer margin, becoming Maize Yellow, Plate 607/2, with basal area Dresden Yellow, Plate 64/2; inside surface—Burnt Orange, Plate 014/3, often marked with Lettuce Green, Plate 861/3 at apex, shading to Majolica Yellow, Plate 09/2, with basal area Dresden Yellow, Plate 64/1. Intermediate petal: outside surface—Chinese Coral, Plate 614/2, grading to Salmon, Plate 412 and then to Buttercup Yellow, Plate 5/2, with basal area Dresden Yellow, Plate 64/1; inside surface—Burnt Orange, Plate 014/3 at apex, becoming Yellow Ochre, Plate 07/2 and grading to Indian Yellow, Plate 6/2, with basal area Dresden Yellow, Plate 64. Inner petal: outside surface—Carrot Red, Plate 612/2 over upper half, with lower portion of petal Dresden Yellow, Plate 64/1; inside surface—Brick Red, Plate 016/2 over upper half of petal, grading to Yellow Ochre, Plate 07/2, and to Dresden Yellow, Plate 64 at base.

This description was made from a rose that was open for 3 days outdoors in the month of August, at West Groove, Pennsylvania, U.S.A.:

*Color.*—Outer petal: outside surface—Salmon, Plate 412/1 around outer margin, grading to Straw Yellow, Plate 604/1, with basal area Dresden Yellow, Plate 64/2; inside surface—Marigold Orange, Plate 11/3, grading to Maize Yellow, Plate 607/2, with basal area Dresden Yellow, Plate 64/2. Inner petal: outside surface—Salmon, Plate 412/2 over upper half of petal, with lower half Straw Yellow, Plate 604/1, with basal area Dresden Yellow, Plate 64/2; inside surface—Marigold Orange, Plate 11/3, grading to Maize Yellow, Plate 607/2, with basal area Dresden Yellow, Plate 64/2.

*General color effect.*—Newly opened flower—Burnt Orange, Plate 014/3, shading into a varying Yellow Ochre, Plate 07/2, to Indian Yellow, Plate 6/2 at center of bloom. 3-days open—Marigold Orange, Plate 11/3 at outer edge of petals, grading to Maize Yellow, Plate 607/2.

*Behavior.*—Drop off cleanly.

*Flower longevity.*—On bush in garden—3 days in August. Cut roses grown outdoors and kept at living-room temperatures—5 days in August.

*Reproductive organs*

Stamens: Medium number; arranged regularly about pistils.

Filaments: Many; most with anthers; medium length. Color—Primrose Yellow, Plate 601.

Anthers: All open at once; medium size; seldom an anther fused with a petaloid. Color—Primrose Yellow, Plate 601/2.

Pollen: From moderate to abundant. Color—gold.

Pistils: Medium number.

Styles: Uneven; medium length; medium heavy; bunched.

Stigma: Color—yellow.

Ovaries: Some protruding from receptacle.

Hips: None observed.

Sepals: Permanent; moderately long; spear-shaped.

Seeds: None observed.

*Plant*

Foliage:

*Leaves.*—Compound of 5 leaflets; normal abundance; medium size; leathery.

*Leaflets.*—Shape—ovoid, with apex acute. Base—obtuse. Margin—simply serrate.

*Color.*—Mature: upper surface—Spinach Green, Plate 0960; under surface—Sage Green, Plate 000861/1. Young: upper surface—Spinach Green, Plate 0960/2, overlaid with Maroon, Plate 1030; under surface—Oxblood Red, Plate 00823/1.

*Rachis (the supporting stem of the compound leaf).*—Medium caliper. Upper side—grooved; hairy. Under side—moderately prickly.

*Stipules.*—Medium length; medium width; with points of medium length turning out at an angle of more than 45°.

*Disease resistance.*—Comparable to that of the average variety grown under the same cultural conditions at West Grove, Pennsylvania, U.S.A.

Growth:

*Habit.*—Bushy; upright; branched.

*Growth.*—Free.

*Canes.*—Medium caliper.

*Main stems.*—Dull. Color—Fern Green, Plate 0862. Prickles—several; color—Fern Green, Plate 0862/3. Hairs—none.

*Branches.*—Dull. Color—Fern Green, Plate 0862. Prickles—several; color—Fern Green, Plate 0862/3. Hairs—none.

*New shoots.*—Dull. Color—Lettuce Green, Plate 861/3, overlaid with Oxblood Red, Plate 00823/3. Prickles—several; color—Oxblood Red, Plate 00823/3. Hairs—none.

What is claimed is:

A new and distinct variety of rose plant of the hybrid tea class, substantially as herein shown and described, characterized particularly as to novelty by the unique combination of a sufficiently vigorous and balanced habit of growth that is suitable for garden decoration, an improved bloom form which is superior to that of the parent varieties, and a distinctive and unique Burnt Orange general color tonality of the flower petals, shading from a varying Yellow Ochre to Indian Yellow at their base.

No references cited.